(12) United States Patent
Sweet et al.

(10) Patent No.: US 7,553,326 B2
(45) Date of Patent: Jun. 30, 2009

(54) METHOD AND APPARATUS FOR PREVENTING DIALYSIS GRAFT INTIMAL HYPERPLASIA

(76) Inventors: Richard M. Sweet, P.O. Box 1010, Kenwood, CA (US) 95452; Robert A. Ganz, 15700 37th Ave. North, Plymouth, MN (US) 55446

( * ) Notice: Subject to any disclaimer, the term of this patent is extended or adjusted under 35 U.S.C. 154(b) by 0 days.

(21) Appl. No.: 10/994,623

(22) Filed: Nov. 22, 2004

(65) Prior Publication Data
US 2005/0113908 A1     May 26, 2005

Related U.S. Application Data

(60) Provisional application No. 60/524,690, filed on Nov. 24, 2003.

(51) Int. Cl.
*A61F 2/06* (2006.01)
(52) U.S. Cl. ............... 623/1.42; 604/8; 623/903
(58) Field of Classification Search ....... 623/1.25–1.54, 623/1.11, 1.13, 23.64, 23.65, 1.1, 903; 424/423–424; 514/2; 604/8
See application file for complete search history.

(56) References Cited

U.S. PATENT DOCUMENTS

| | | | |
|---|---|---|---|
| 4,512,762 A * | 4/1985 | Spears .................. | 604/21 |
| 5,505,946 A | 4/1996 | Kennedy | |
| 5,571,152 A | 11/1996 | Chen et al. | |
| 5,629,077 A * | 5/1997 | Turnlund et al. ........... | 623/1.15 |
| 5,658,894 A | 8/1997 | Weisz | |
| 5,702,432 A * | 12/1997 | Chen et al. ................ | 607/88 |
| 5,786,326 A | 7/1998 | Horwitz | |
| 5,874,419 A | 2/1999 | Herrmann | |
| 5,902,799 A | 5/1999 | Herrmann | |
| 5,935,940 A | 8/1999 | Weisz | |
| 6,054,449 A | 4/2000 | Robinson et al. | |
| 6,087,552 A | 7/2000 | Gregory | |
| 6,096,030 A | 8/2000 | Ortiz | |
| 6,136,798 A | 10/2000 | Cody | |
| 6,159,236 A | 12/2000 | Biel | |
| 6,273,913 B1 | 8/2001 | Wright et al. | |
| 6,306,166 B1 | 10/2001 | Barry et al. | |
| 6,335,029 B1 * | 1/2002 | Kamath et al. .............. | 424/423 |
| 6,366,719 B1 | 4/2002 | Heath et al. | |
| 6,416,531 B2 | 7/2002 | Chen | |

(Continued)

OTHER PUBLICATIONS

U.S. Appl. No. 10/298,724, Ganz et al.

*Primary Examiner*—Brian E. Pellegrino
(74) *Attorney, Agent, or Firm*—James V. Harmon

(57) ABSTRACT

To prevent intimal hyperplasia within a dialysis graft, a flexible tube comprising the dialysis graft is coated interiorly before placement with an anticarcinogen or mitosis-inhibiting agent for preventing cell division. The graft can also be irradiated with light energy by directing light into the lumen of the tube that has been grafted in place, thereby preventing or reducing dialysis graft intimal hyperplasia and reducing inflammation. The light source can be a light emitting diode (LED) or a chemical light source, i.e., a chemiluminescent substance for producing cool light energy within the graft to prevent or reduce the symptoms of GIH. When phototherapy is used, the body is exposed to light radiation at the site of the graft in sufficient amount to prevent undesired cell proliferation within the vessels, the graft, or surrounding tissue where the invention is used without detectable damage to body tissue.

8 Claims, 2 Drawing Sheets

U.S. PATENT DOCUMENTS

| | | | |
|---|---|---|---|
| 6,520,981 B1 | 2/2003 | LaMuraglia | |
| 6,602,274 B1 | 8/2003 | Chen | |
| 6,605,115 B1 | 8/2003 | Cooke | |
| 6,609,014 B1 | 8/2003 | Allison | |
| 6,623,513 B2 * | 9/2003 | Biel | 607/88 |
| 6,689,803 B2 | 2/2004 | Hunter | |
| 6,699,260 B2 | 3/2004 | Dubrul | |
| 6,726,923 B2 | 4/2004 | Iyer | |
| 6,764,501 B2 | 7/2004 | Ganz | |
| 6,821,289 B2 | 11/2004 | Bode | |
| 6,827,926 B2 | 12/2004 | Robinson | |
| 6,852,122 B2 * | 2/2005 | Rush | 623/1.13 |
| 6,867,235 B2 | 3/2005 | Mazur | |
| 6,887,862 B2 | 5/2005 | Rychnovsky | |
| 6,899,723 B2 | 5/2005 | Chen | |
| 6,918,869 B2 * | 7/2005 | Shaw et al. | 600/3 |
| 6,926,735 B2 * | 8/2005 | Henderson | 623/1.42 |
| 7,008,397 B2 * | 3/2006 | Tweden et al. | 604/8 |
| 7,107,996 B2 | 9/2006 | Ganz | |
| 2002/0065546 A1 * | 5/2002 | Machan et al. | 623/1.13 |
| 2002/0146369 A1 | 10/2002 | Goldenberg | |
| 2002/0183301 A1 | 12/2002 | Rychnovsky | |
| 2003/0008857 A1 | 1/2003 | Hunt | |
| 2003/0065382 A1 * | 4/2003 | Fischell et al. | 623/1.15 |
| 2003/0073679 A1 | 4/2003 | Mody | |
| 2003/0082101 A1 | 5/2003 | Taylor | |
| 2003/0105357 A1 | 6/2003 | Mazur | |
| 2003/0181894 A1 | 9/2003 | Neuberger | |
| 2003/0212443 A1 | 11/2003 | LaMuraglia | |
| 2004/0208855 A1 | 10/2004 | Allison | |
| 2004/0236275 A1 * | 11/2004 | Pruitt et al. | 604/96.01 |
| 2005/0004510 A1 | 1/2005 | Chen | |
| 2005/0112131 A1 | 5/2005 | Pogue | |
| 2005/0130950 A1 | 6/2005 | Rychnovsky | |
| 2005/0136102 A1 | 6/2005 | Hoffman et al. | |

* cited by examiner

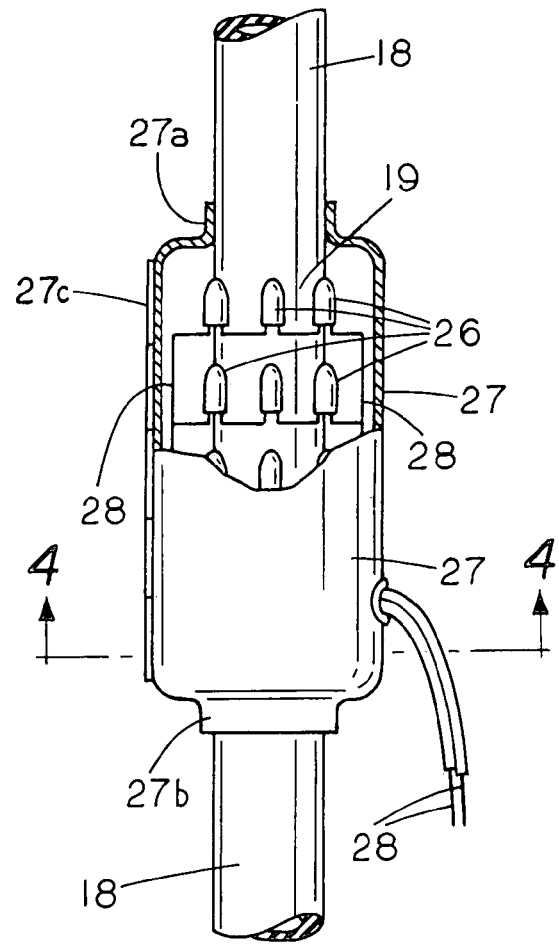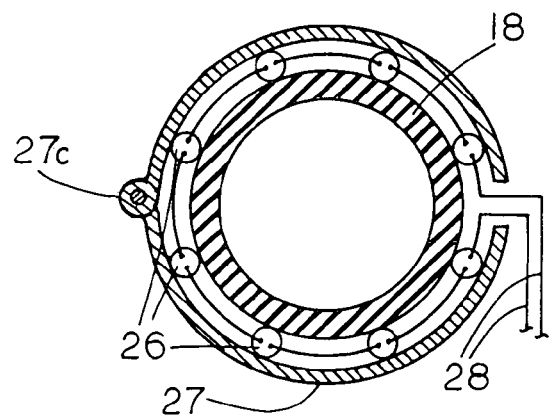

METHOD AND APPARATUS FOR PREVENTING DIALYSIS GRAFT INTIMAL HYPERPLASIA

The present application claims the benefit of provisional application No. 60/524,690, filed Nov. 24, 2003, and entitled, Method and Apparatus for Preventing Dialysis Graft Intimal Hyperplasia.

FIELD OF THE INVENTION

The present invention relates to the medical arts and more particularly to the prevention of intimal hyperplasia.

BACKGROUND OF THE INVENTION

When an artificial blood vessel, i.e., a graft, is connected between an artery and a vein to act as a shunt, a tubular polytetraflouroethylene graft is commonly used. However, many patients with a graft of this kind develop dialysis graft intimal hyperplasia (GIH), a condition in which cells lining the vessels grow at a high rate thereby blocking the vessel. Although efforts have been made to reduce or eliminate hyperplasia of the dialysis graft, none of the proposed solutions have been entirely satisfactory.

Various attempts have been made to address this problem. For example, U.S. Pat. Nos. 5,658,894; 5,786,326; 5,874,419; 6,136,798; 5,935,940; 5,902,799; 6,605,115; 6,689,803 and 6,726,923 describe drugs, biologicals and other pharmaceutical preparations that can be used for treating intimal hyperplasia, but these substances must be taken internally or applied to the occluded vessel. Consequently, these treatments have the potential for producing an allergic reaction, side effects, or anomalous results. Other approaches have been taken, for example, U.S. Pat. No. 6,669,260, describes an invasive procedure in which the occlusion is surgically aspirated from the vessel. Surgical procedures are characteristically more costly, require greater expertise and may have to be repeated periodically. The methods of treatment described in the patents are therefore not entirely satisfactory. Consequently, the need still exists for a more effective system for treating intimal hyperplasia.

In view of these and other shortcomings of the prior art, it is one objective of the present invention to provide a new method and apparatus for preventing dialysis graft intimal hyperplasia which is well tolerated by the patient and which does not cause discernable damage to surrounding body tissue.

Another object of the invention is to provide a new method and apparatus of the type described which can be readily produced at a reasonable cost and is suited for wide scale use and distribution.

Another objective of the invention is to provide a new method and apparatus of the type described which can be carried out effectively while a surgical procedure is being performed, typically, in about 1-2 hours.

Yet another objective of the invention is to provide a new method and apparatus of the type described which can be provided in a compact package that is small enough to be attached to or carried by the patient without undue discomfort or inconvenience.

These and other more detailed and specific objects of the present invention will be better understood by reference to the following figures and detailed description which illustrate by way of example but a few of the various forms of the invention within the scope of the appended claims.

SUMMARY OF THE INVENTION

In certain surgical procedures, such as placement of a hemodialysis shunt, an artificial blood vessel, is grafted between an artery and a vein to provide access to the circulatory system. This graft normally consists of a plastic tube or the like, e.g., a polytetraflouroethylene tube is typically used. Briefly, to prevent intimal hyperplasia within and proximate to the plastic tube in accordance with the present invention, the flexible plastic tube is coated interiorly before placement with an agent for preventing cell division, e.g., an anticarcinogen or other mitosis inhibiting drug to be described in more detail below for preventing cell division or growth. The graft can also be radiated with light energy or light energy can be used alone so as to direct light into the interior of the tubular shunt for reducing inflammation and preventing or reducing dialysis graft intimal hyperplasia. The light source can, for example, be a light emitting diode (LED) or a chemical light source, i.e., a chemiluminescent substance for transmitting cool light energy into body tissue to prevent or reduce the symptoms of GIH. In accordance with the invention, the graft is exposed to light radiation in a sufficient amount to prevent undesired cell proliferation within the vessels, graft and surrounding tissue without detectable damage to body tissue. In one preferred form of the invention, visible blue or red light or the combination of them is employed. Blue and red light can be provided by an incandescent lamp or other suitable lamp, an LED, a laser or chemical light source with preferred wavelengths predominantly between about 300 nm to about 800 nm.

BRIEF DESCRIPTION OF THE DRAWINGS

FIG. 3 is an elevational view partly in section of the light irradiation unit shown in FIG. 1 on a larger scale.

FIG. 4 is a cross-sectional view taken on line 4-4 of FIG. 3 on a slightly larger scale.

DETAILED DESCRIPTION OF THE INVENTION

Figure 1:
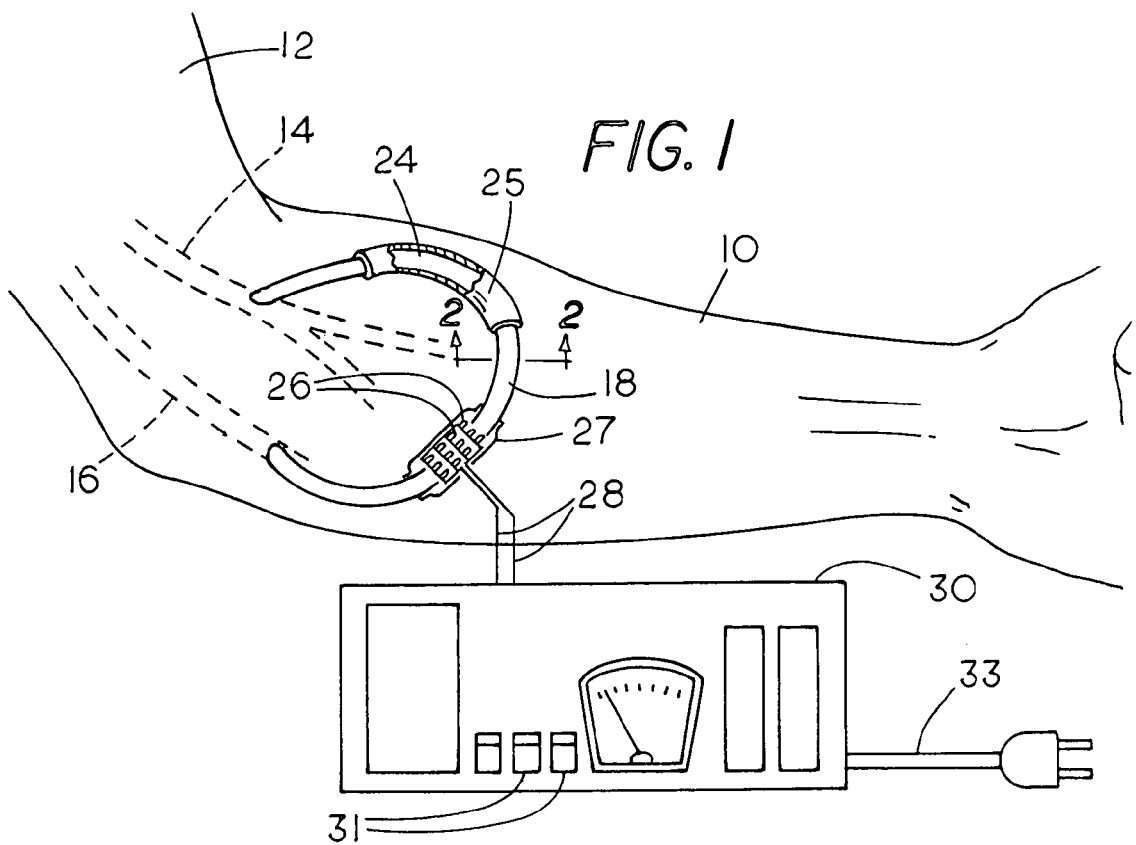
FIG. 1 is a side elevational view showing a dialysis graft according to the invention placed on the forearm of the patient.

The present invention provides a method and apparatus for the avoidance and treatment of intimal hyperplasia and is especially well suited for use in hemodialysis grafts or access. Dialysis graft intimal hyperplasia (GIH) occurs in a large segment of the hemodialysis (HD) population and is the cause of significant cost, morbidity and mortality in the HD population. Greater than 50% of HD patients in many areas have expanded polytetraflouroethylene (PTFE) grafts.

In accordance with the present invention, the PTFE graft is coated before placement with an anticarcinogen or other agent for preventing cell division or growth. Thus, intimal hyperplasia, brought about by various growth factors, is inhibited in accordance with the invention by drugs such as, but not limited to, sirolimus as well as other agents for controlling cell division as described more fully below. The graft can also be provided with a source of light energy arranged to direct light onto the graft for reducing inflammation and thereby preventing GIH. Phototherapy thus prevents cell division through the application of visible light and similar modalities at the time of engraftment or during angioplasty of the stenotic area in treating intimal hyperplasia and graft stenosis.

The vast majority of dialysis patients in the United States undergo hemodialysis for treatment of chronic renal failure. Maintaining a patent access is of paramount importance in this group of patients. Only approximately 50-80% of patients using a PTFE shunt have patency at two years. Because most patients have poor native vessels, artificial graft material in many instances is the mode of choice for chronic vascular access. Approximately 0.5-0.8 episodes of fistula thrombosis occur per patient year of those on dialysis. Most frequently this results from venous outflow obstruction. Approximately 75% of all thromboses are associated with stenotic lesions in the venous system at the point of anastomosis.

Surgical thrombectomy, lytic therapy, balloon angioplasty and surgical graft replacement are the most common treatments for venous stenosis. All these are associated with great cost, morbidity and on occasion mortality. Therefore, primary prevention of venous stenosis is a major therapeutic event in the management of hemodialysis patients.

Venous stenosis is a result of multiple factors including an inflammatory response at the anastomotic site including vascular growth factors, platelet-derived growth factor, basic fibroblast growth factor and transforming growth factor. It has been shown in the use of drug-eluting coronary stents that there is mitigation of these factors, and therefore much lower restenosis rates compared to non-drug coated stents. According to the present invention, a coating comprising an agent for preventing cell growth or division is applied to and most preferably is provided within the dialysis graft material itself. The coating comprises at least one anticancer drug or other agent that regulates cell proliferation and/or growth such as, but not limited to, paclatexel, sirolimus, taxol and methotrexate to prevent in growth and stenosis in the dialysis graft. Blue light phototherapy is used to augment and treat graft prophylactically and at the time of intervention for venous stenosis. Phototherapy applied in this manner has been demonstrated to inhibit cell growth at specific endovascular and enteric sites.

Figure 2:
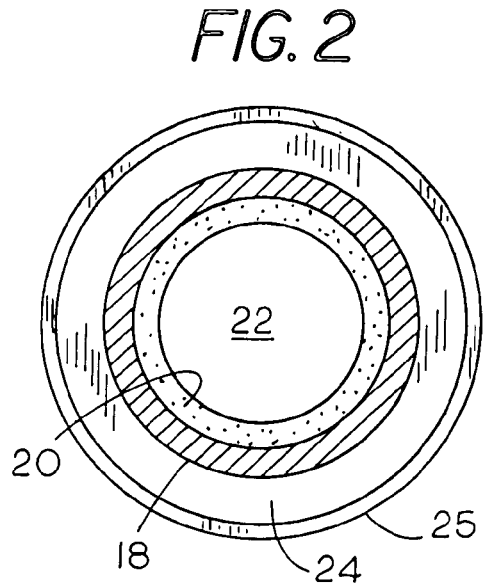
FIG. 2 is a cross-sectional view on a larger scale taken on line 2-2 of FIG. 1.

Refer now to the Figures which illustrate the invention by way of example. Shown in FIGS. 1 and 2 is one of the most common types of arteriovenous grafts. The forearm is indicated at 10, the upper arm at 12, the brachial artery at 14 and the basilic vein at 16. A loop graft 18 is formed from a short section of PTFE tubing which is grafted surgically as shown to provide an arteriovenous anastomosis. The PTFE tube is used conventionally in this example as a hemodialysis graft in the treatment of kidney disease.

The graft 18 includes an inner drug eluting coating or layer 20 (FIG. 2) which is impregnated with the cell growth regulator described above. The coating 20 can comprise any suitable biocompatible matrix such as a plastic resin, elastomer or hydrophilic gel. The coating 20 can, for example, be a matrix that is formed from any of the commercially available implantable compositions that are used for providing a gradual release of a madicment, e.g., the same composition in Norplant® implantable hormone releasing strips that are used in birth control. The drug-eluting matrix 20 can, for example, compromise a copolymer of dimethylsiloxane and methyl vinyl siloxane which is sold by Dow Corning, Inc. under the trademark Silastic®. The cell division inhibiting agent can be dispersed in the matrix 20 at a concentration of about 0.1% to about 65% by weight. To prevent thrombus formation, the matrix can also include an anticoagulant, e.g., heparin in the amount of about 0.05% to about 10% by weight.

Other suitable cardiovascular implant polymers include polyurethane, polyurethane/silicone copolymers (Elast-Eon® by AorTech Intl PLC)+, and silicone rubber. Erodible matrix polymers which are biocompatible include Vicryl®, a polylactic acid/polyglycolic acid copolymer. Other erodible bio-implantible matrix polymers include polyortho esters, poly(alpha-hydroxy ester)s, and polyanhydrides. Synthetic matrix bio-erodible polymers also include tyrosine-derived polycarbonates and polyacryaltes, lactide based polydepsipeptide polymer, poly(L-lactic acid-do-L-aspartic acid), and lactide based poly(ethylene glycol).

The matrix 20 acts as a carrier for the sustained release of the cell-growth control agent at a selected rate into the blood passing through the lumen 22 of the graft 18. The drug-filled matrix 20 can extend throughout the entire length of the loop graft 18 including the end portions which are sutured to the native blood vessels 14 and 16. As the control agent is continuously released from the inner layer 20 of the graft 18, the undesirable cell growth and stenosis in the dialysis graft that formerly occurred is either entirely eliminated or reduced to a tolerable level. Optionally, the coating 20 is also applied to the outside surface of the graft 18.

In accordance with the present invention, light energy is used with the chemotherapeutic treatment described above or by itself to reduce or eliminate hyperplasia. The light energy applied to the graft can be any suitable visible light, especially red light or blue light in the range of 300-500 nm peaking about 400 nm to 430 nm. When red light is used, it typically has a wavelength in the range of about 600-800 nm with a peak in the range of about 630-650 nm. A combination of blue and red light can also be used.

Light can be provided by various light sources including light emitting diodes. While suitable LED's that are capable of producing visible light in any portion of the spectrum can be employed, wavelengths in a range of from about 300-500 nm and especially in range of about 400-430 nm are preferred. When the power supply consists of batteries, only a fraction of the watt will be produced but if an external power supply (30) is provided, the LED's can produce several watts of power. Luminous flux that results is capable of penetrating the entire graft. Any suitable commercially available power supply 30 can be used. Current is supplied by a power cord 33 and power is controlled by switches 31.

The use of visible light is especially effective because mobile proliferating cells absorb the blue or red light energy and in the presence of oxygen, free radicals are then generated which are believed to be ultimately responsible for the death or debilitation of the proliferating cells through apoptosis, necrosis or from other causes. Red light also decreases inflammation by acting directly on the surrounding tissue.

In accordance with the present invention, light can be provided by any of several different light sources including but not limited to incandescent light sources, gas discharge tubes, light emitting diodes (LED), laser diodes, chemiluminescent sources, mercury vapor tubes and other light sources known in the art. Light emitting diodes and chemiluminescent sources are particularly useful because they are capable of producing cool light, i.e., light that does not generate sensible heat. When a chemiluminescent source is used, the light can be transmitted directly onto and within the graft as long as required to accomplish the desired treatment, typically for the length of a surgical procedure that is being performed, e.g., about 1-1.5 or 2 hours.

As shown in FIGS. 1 and 2, the graft 18 is provided with an outer coating 24 for producing light through photogenesis, i.e., phosphorescence or chemical light, to inhibit cell division through phototherapy for the purpose of treating the graft prophylactically as well as at the time of interventions for venous stenosis. The coating 24 can be any of the commercially available photoluminescent compounds, preferably those that produce visible light and especially light in the blue spectral range for reducing or entirely preventing undesired cell growth and stenosis in the dialysis graft. Surrounding the coating 24 is a light reflector 25 comprising an aluminized plastic film for reflecting all light radiation centrally into the lumen of the tubing 18. The luminescence provides cool light radiation that penetrates to the interior of the tubing 18 through coating 20 for preventing cell proliferation within the graft and adjacent vessels or other tissue in the same manner described hereinabove and is allowed to provide light radiation therapy until light is no longer produced. An advantage of using a chemical or chemiluminescent liquid is that light radiation of a cool variety produces the desired therapeutic effect but since little if any heat is produced which can be sensed, there will be no damage to the surrounding tissue of the patient. A variety of chemiluminescence substances can be employed such as luminal and lucigenin. Among the preferred light producing chemicals are the oxilaic ester and hydrogen peroxide with an efficient fluorescer and catalyst as disclosed in U.S. Pat. No. 3,597,362, which is incorporated herein by reference.

Other kinds of fluorescent compounds include: the conjugated polycyclic aromatic compounds examples of which are anthracene, benzanthracene, phenanthrene, naphthacene, pentacene, perylene, perylene violanthrone, and the like and their substituted forms.

Typical substituents for all of these are phenyl, lower alkyl (C.sub.1-C.sub.6), chloro, bromo, cyano, alkoxy (C.sub.1-C.sub.16), and other like substituents which do not interfere with the light-generating reaction can be used.

The preferred fluorescers include 9, 10-bis(phenylethynyl) anthracene, 1-methoxy-9, 10-bis (phenylethynyl) anthracene, perylene, 1,5-dichloro 9, 10-bis(phenylethynyl) anthracene, rubrene, monochloro and dichloro substituted 9,10-bis(phenylethynyl) anthracene, 5,12-bis (phenylethynyl) tetracene, 9,10-diphenyl anthracene, and 16,17-dihexyloxyviolanthrone.

The lifetime and intensity of the chemiluminescent light emitted can be regulated by the use of certain regulators such as: (1) by the addition of a catalyst, which changes the rate of reaction of hydroperoxide. Catalysts which accomplish that objective include those described in M. L. Bender, Chem. Revs., Vol. 60, p. 53 (1960). Catalysts can also be used which alter the rate of reaction or the rate of chemiluminescence including those accelerators of U.S. Pat. No. 3,775,366, and decelerators of U.S. Pat. Nos. 3,691,085 and 3,704,231, or (2) by the variation of hydrogen peroxide. Both the type and the concentration of hydrogen peroxide are critical for the purposes of regulation.

Of the catalysts tried, sodium salicylate and various tetraalkylammonium salicylates have been the most widely used. Lithium carboxylic acid salts, especially lithium salicylate, lithium 5-t-butyl salicylate and lithium 2-chlorobenzoate are excellent catalysts for low temperature hydrogen peroxide/oxalate ester/fluorescer chemiluminescent systems.

Chemical light can be produced by a mixture of reagents, e.g., an oxalate ester and hydrogenperoxide together in the presence of a catalyst and a fluorescer. Typically, fluorescers are chosen that are peroxide stable to provide a long lasting glow. In most instances, a single fluorescer has been used to produce a particular colored light. In some cases, two or more fluorescers of essentially equivalent stability in peroxide have been mixed to produce a blended color. As an example, a blue emitting fluorescer will be mixed with a red emitting fluorescer to make a pink light.

Of the numerous fluorescers described herein, relatively few emit light in peroxyoxalate chemiluminescence and are sufficiently peroxide stable (five phenylethynyl anthracenes, one violanthrone, and three perylene dicarboximides) to yield commercially viable products. While other fluorescers are known to emit light, they are not peroxide stable and have historically been rejected for commercial use (see U.S. Pat. No. 6,267,914). All publications and patents are herein incorporated by reference to the same extent as if each individual publication or patent was specifically and individually indicated to be incorporated by reference.

A light source comprising several light emitting diodes 26 will now be described in more detail with reference to FIGS. 1, 3 and 4. As shown in the Figures, the graft tubing 18 is surrounded by several light emitting diodes 26 which are connected by suitable electrical conductors 28 to the power supply 30. The diodes 26 are contained in a light reflective metal casing 27 about 1-2 cm in diameter which is secured to the graft tubing 18 at 27a and 27b. A portion of the tubing 18 within the casing 27 can be formed from glass or other transparent material 19 to enhance light transmission into the interior of tubing 18. If desired, the casing 27 can be provided with a longitudinal hinge 27c along one side to enable the casing and diodes 26 which are attached to its inside surface to be removed from the tubing whenever the need arises. When the diodes 26 are energized, they produce cool light, most preferably in the blue range of the spectrum to provide phototherapy for assisting in the treatment of the graft prophylactically or at the time of intervention so as to reduce or eliminate the symptoms of unwanted cell growth and stenosis in the hemodialysis graft. Other light sources can be used, such as incandescent light sources but are not preferred because of the heat produced. The phototherapy will thus inhibit undesired cell growth at specific endovascular and enteric sites where the light sources 24 or 26 are located as well as in the surrounding tissue into which the light penetrates. The light emitting coating 24 and the light sources 26 while shown to cover only a segment of the graft 18, can, if desired, extend the entire length of the graft including the ends that are attached to the artery 14 and vein 16.

Each light emitting diode 26 has a semiconductor chip (not shown) connected to one electrical contact and a contact wire which extends from the chip to one of the other electrical contacts. When treatment is to begin, current is supplied to the conductors 28 causing the LED's to provide light of a selected spectral range, most preferably blue light in the range between about 300-500 nm or red light of about 600-800 nm or a combination thereof. An important advantage of the LED's is their ability to provide cool light radiation that is highly effective in preventing hyperplasia in the graft and surrounding vessels without damaging the tissue of the patient. The LED's are turned on and allowed to remain in operation for a period of time required for effective treatment, typically 1-2 hours. If desired, the LED's can be replaced by a light emitting plastic (LEP) in which the semiconducting material is organic. Any suitable commercially available organic semiconducting material such as a PPV light emitting polymer or derivative thereof can be used. During use, the chemical composition of the PPV polymer changes with associated changes in physical and electrico-optical properties that produce light radiation. Laser diodes can be used in place of LED's if desired. It should be understood that the invention is not limited to specific apparatus or methods described and can be used with various other devices, fabrication methods, arrangements, systems and methods of employment which irradiate the graft and surrounding body tissues.

While the exact mode of operation is not known with certainty, it is believed that the phototherapeutic light radiation retards cell division of the endothelial cells that would otherwise proliferate from the areas where the graft is sutured to the vessel resulting in intimal hyperplasia of the graft 18. When used with the coating 20, the light energy can act synergistically by killing off cells already weakened by the cell-growth inhibiting substance in the coating 20. Thus, by preventing unwanted cell proliferation, stenosis of the graft is avoided.

The utility of the present invention in the treatment of GIH is important not only in reducing undesired cell proliferation, but also because the administration of light energy is useful in itself for reducing inflammation of the tissue. It appears that the exposure of body tissue to light energy such as visible blue light or red light, or the combination helps to reduce inflammation of the vascular tissue in and around the graft. The present method of treatment is therefore important because a reduction in vascular inflammation per se can be helpful in reducing or eliminating symptoms of the disease. The reduction of inflammation as disclosed herein is also beneficial because reducing inflammation will decrease the presence of inflammatory cytokines and inflammatory chemokines. In addition, it can also reduce the presence of acute phase reactants and soluble adhesion molecule TLR4 receptor activity which is beneficial to the patient. Thus, the present invention can be used to decrease the expansion of adhesion molecules, reduce proliferation of smooth muscle cells and activate immune cells which help to reduce or eliminate the symptoms of vascular inflammatory disease.

The coatings 20 used in the invention will be better understood by reference to the following examples:

| MATRIX | PERCENT BY WEIGHT OF CELL GROWTH INHIBITOR | | |
|---|---|---|---|
| Hydrophilic Gel Matrix[1] | Example 1 2% paclataxel | Example 2 4% paclataxel | Example 3 20% paclataxel |
| | Example 4 0.5 sirolimus | Example 5 3% sirolimus | Example 6 65% sirolimus |
| Silicone Rubber[2] | Example 7 0.2% taxol | Example 8 6% taxol | Example 9 21% taxol |
| | Example 10 0.4% methotrexate | Example 11 3% methotrexate | Example 12 24% methotrexate |
| Polyurethane | Example 13 0.1% methotrexate | Example 14 5% methotrexate | Example 15 18% methotrexate |
| | Example 16 1% paclataxel | Example 17 6% paclataxel | Example 18 15% paclataxel |

[1]Crosslinked polyethylene oxide/polyurethane copolymer 2-10% by weight, propylene glycol 2-5% by weight and water 85-96% by weight.
[2]Copolymer of dimethylsiloxane and methyl vinyl siloxane.

Many variations of the present invention within the scope of the appended claims will be apparent to those skilled in the art once the principles described herein are understood.

What is claimed is:

1. A method of reducing or eliminating dialysis graft intimal hyperplasia of a human or animal patient that is adapted for hemodialysis graft access in the treatment of kidney disease comprising,
   providing a polymeric tube that is flexible throughout and is a) comprised of a material adapted for surgical grafting at both ends thereof, b) constructed and arranged to permit access throughout to the patient's blood and c) formed from a material that is transparent to light energy to thereby enable visible light to be directed therethrough for exteriorly irradiating blood cells proliferating within the tube to kill or debilitate the cells and having a pair of ends for circulating blood between blood vessels of the patient,
   applying an erodible biocompatible coating matrix to an interior surface of the tube, said erodible matrix having a cell-division inhibiting agent consisting essentially of an anticarcinogen dispersed therein that during use is in direct contact with the blood of the patient,
   surgically grafting the tube between the patient's native blood vessels such that said tube thereby comprises a loop graft forming a shunt which replaces a portion of said blood vessel by being grafted thereto at each of said ends for enabling the blood to circulate through the tube from one of the patient's vessels to another,
   controlling delivery of the agent into a central lumen of the tube at selected rate that is the sustained release rate of the erodible matrix that is used,
   exposing the mobile proliferating cells responsible for graft intimal hyperplasia to cool red or blue visible light, said light being characterized by the absence of sensible heat thereby preventing damage to surrounding tissue, the exposure to light being carried out in the presence of oxygen to cause destruction of the proliferating cells consisting essentially of apoptosis or necrosis of the cells resulting from the treatment of the cells by the red or blue light while exposing proliferating cells within the tube to said cell-division inhibiting agent to reduce or eliminate one or more of the symptoms of dialysis graft intimal hyperplasia.

2. The method of claim 1 including the step of providing a light source selected from the group consisting of a chemiluminescent source, an incandescent source, a gas discharge tube, a mercury vapor tube, a laser, and a diode and directing light from the light source onto the graft tubing.

3. The method of claim 1 including the step of providing said light energy within the range of about 300-500 nm.

4. The method of claim 1 wherein the agent is selected from the group consisting of paclatexel, sirolimus, taxol and methotrexate.

5. The method of claim 1 wherein the agent is dispersed in a matrix comprising a member selected from the group consisting of a plastic resin, an elastomer and a hydrophilic gel.

6. The method of claim 1 including the step of placing proximate the tube as the light source at least one light emitting diode and a light reflective surface is provided adjacent the diode for reflecting light from the diode into the tube.

7. The method of claim 1 including removably connecting the light source to the tube and including a reflector for directing light from the light source into the tube.

8. The method of claim 1 including the step of providing as the source of light a phosphorescent substance that is optically coupled to the tube for directing light energy into the lumen of the tube.

* * * * *